(12) United States Patent
Kumar et al.

(10) Patent No.: US 9,488,513 B2
(45) Date of Patent: Nov. 8, 2016

(54) FLEXIBLE FLUID LEVEL SENSOR WITH IMPROVED MEASUREMENT CAPABILITY

(71) Applicant: Molex, LLC, Lisle, IL (US)

(72) Inventors: Arun Kumar, Fremont, CA (US);
Steven John Fulton, Elgin, IL (US)

(73) Assignee: Molex, LLC, Lisle, IL (US)

( * ) Notice: Subject to any disclaimer, the term of this patent is extended or adjusted under 35 U.S.C. 154(b) by 20 days.

(21) Appl. No.: 13/705,375

(22) Filed: Dec. 5, 2012

(65) Prior Publication Data

US 2014/0152323 A1   Jun. 5, 2014

(51) Int. Cl.
*G01R 27/26* (2006.01)
*G01F 23/00* (2006.01)
*A61M 5/168* (2006.01)

(52) U.S. Cl.
CPC ............ *G01F 23/00* (2013.01); *A61M 5/1684* (2013.01); *A61M 2205/3317* (2013.01); *A61M 2205/3389* (2013.01)

(58) Field of Classification Search
CPC ............ G01F 23/00; A61M 2205/3389; A61M 5/1684; A61M 2205/3317
USPC ................................. 324/658–690
See application file for complete search history.

(56) References Cited

U.S. PATENT DOCUMENTS

| | | | |
|---|---|---|---|
| 5,861,811 A * | 1/1999 | Lease et al. | 340/618 |
| 6,490,920 B1 | 12/2002 | Netzer | |
| 7,037,277 B1 * | 5/2006 | Smith et al. | 600/584 |
| 7,258,005 B2 * | 8/2007 | Nyce | 73/304 C |
| 8,393,209 B2 | 3/2013 | Thibault | |
| 2003/0000303 A1 * | 1/2003 | Livingston | G01F 23/268 73/304 C |
| 2005/0246672 A1 * | 11/2005 | Bois et al. | 716/5 |
| 2008/0134779 A1 * | 6/2008 | Tung | G01F 23/24 73/304 C |
| 2012/0256642 A1 * | 10/2012 | Badaye et al. | 324/658 |

FOREIGN PATENT DOCUMENTS

| | | |
|---|---|---|
| CN | 101472454 A | 7/2009 |
| DE | 10-2004-04442 A1 | 8/2005 |
| KR | 2011-0120849 A | 11/2011 |

* cited by examiner

*Primary Examiner* — Farhana Hoque
(74) *Attorney, Agent, or Firm* — James A. O'Malley

(57) ABSTRACT

A capacitive fluid sensor is provided that utilizes a flexible substrate. It has a plurality of conductive members supported on it which are connected to a connecting end. The conductive members are arranged in an array and are aligned with a longitudinal axis of the substrate and the members are separated by intervening spaces. The intervening spaces are arranged so that they cross the longitudinal axis at an angle such that adjacent conductive members overlap each other when viewed from a side edge of the sensor. Such an arrangement provide more accurate measurement of fluid levels within containers.

39 Claims, 4 Drawing Sheets

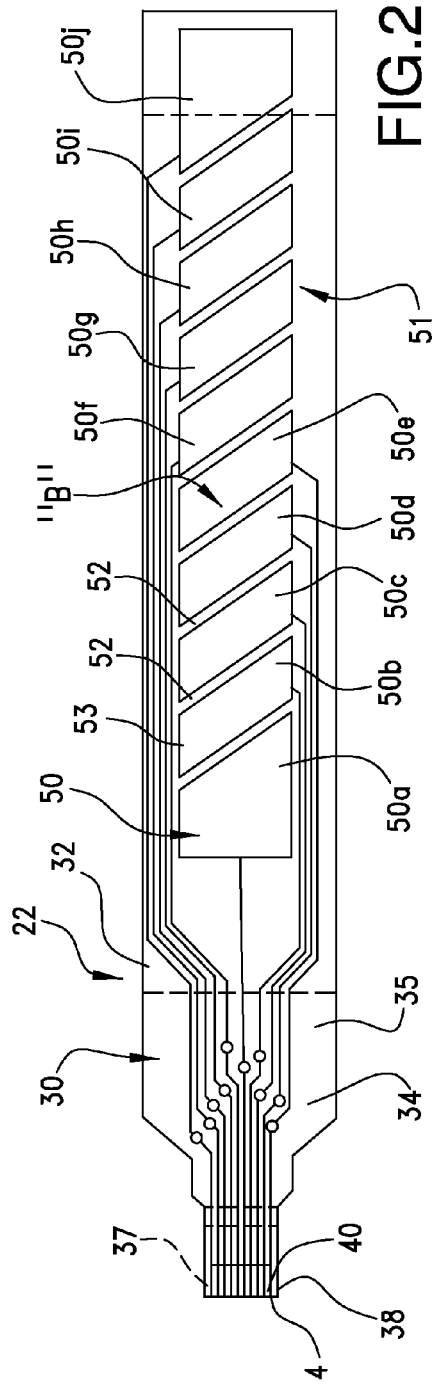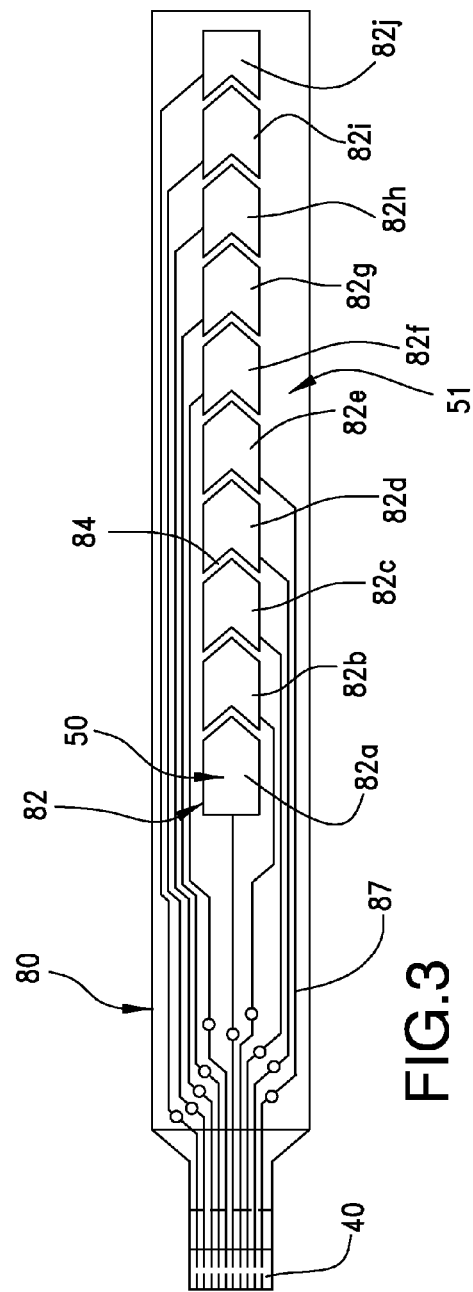

FLEXIBLE FLUID LEVEL SENSOR WITH IMPROVED MEASUREMENT CAPABILITY

BACKGROUND OF THE PRESENT DISCLOSURE

The Present Disclosure relates generally to fluid sensors, and, in particular, to sensors that have a flexible body for application to fluid containers of varying configurations, as well as sensors that have improved sensor capabilities.

Fluid sensors are used in a variety of applications. Their usage in the medical arts has grown, and sensors are used in association with biopumps that remove a certain volume of fluid from a body location, with containers such as beakers, columns and drip bags, to measure predetermined levels of fluid for infusion into the body. Other applications are known, and many of these fluid containers have irregularly-shaped exterior configurations, making it difficult to read the measurements scribed on their sides. Optical measurement indicia, such as graduated lines, are hard to difficult to read in an automated manner, and are not conducive to fast timing diagnostic and other procedures. Hence, fluid sensors were developed that may be attached to containers and which can provide readout signals that may be displayed, or otherwise read, by a monitoring device.

Such a fluid sensor is described in U.S. Pat. No. 6,490,920, issued 10 Dec. 2002, the content of which is hereby incorporated herein in its entirety. The sensor described in the '920 patent utilizes a flexible substrate that supports a series of conductive members disposed on a surface of the substrate and are arranged to form a single sensor with multiple, interacting members, more in the form of appendages that extend in opposite directions from a baseline of each such member. These appendages are interlaced with each other so that they appear as a series of fingers that extend into gaps between adjacent fingers of an opposite member. As such, each member of the sensor of the '920 patent constitutes one single and elongated sensor member. The large length of this sensor reduces its ability to accurately, at very small tolerances measure fluid levels. Although it is suitable for a gross measurement, it is difficult to obtain very fine tolerance fluid level readings. The Present Disclosure is therefore directed to an improved fluid sensor better suited for capacitively measuring fluid levels in containers, and particularly irregularly shaped containers.

SUMMARY OF THE PRESENT DISCLOSURE

Accordingly, there is provided an improved fluid level sensor that has a better tolerance, resulting in finer measurements for exterior measurement of fluids held within a container.

In accordance with an embodiment as described in the following disclosure, a sensor comprises a flexible substrate, provided as an elongated strip. A plurality of conductive portions, members or electrodes are disclosed, each of which has a plate-like configuration which is supported on the substrate. The conductive members are arranged in an array, each array containing a desired number of distinct conductive members. The members are separated from each other by a plurality of intervening spaces and each such conductive member has a conductive trace connected to it, which extends from the conductive member longitudinally along the substrate to a connecting end of the substrate where it joins a contact pad. These contact pads provide points of connection for the sensor so that the sensor may be inserted into a connector and connected to circuitry of a readout or processor operatively connected to a display means. The substrate includes multiple layers with a thin polyester layer supporting the conductive members thereon, which may easily be applied thereto by way of printing or the like. A cover layer of polyester or other suitable material may be provided to seal the conductive members in place, and a layer of pressure-sensitive adhesive may be applied to a mounting side of the substrate.

The conductive members are further configured such that all but two of the members, those lying at the opposing ends of the array, are of the same configuration. In other words, the conductive members that are included between the second, and the second to last, conductive member (or "penultimate" members) are substantially identical in configuration. In one embodiment, the conductive members may include four-sided members that are oriented on the substrate at an angle respect to a longitudinal axis of the substrate, such that the intervening spaces separating the conductive member extend at angle to the longitudinal axis and, and intersect the longitudinal axis at an angle thereto. In this manner, when a point of reference is taken that is normal to the substrate longitudinal axis, the conductive members, in effect, overlie each other and any line drawn within any of these included conductive members that is normal to the substrate longitudinal axis and within the end boundaries of conductive members will contact two adjacent conductive members.

As the conductive members are separated by their associated intervening spaces, each such conductive member becomes a single sensor in the array, having a given measurement tolerance between the ends, in a lengthwise direction of each conductive member. These single sensors may be made with a given tolerance, such as 5%, and the use of multiple sensors, each with a 5% tolerance within its boundaries will provide a tolerance of 0.05% over the entire length of the sensor.

In another embodiment of the Present Disclosure, the conductive members have a configuration similar to that of a chevron, so that the intervening spaces between adjacent conductive members are angled in a non-linear manner, meaning that they extend in different directions as between adjacent conductive members, so that there is a similar overlap of adjacent sensors occurs in a normal direction as mentioned above with respect to the first embodiment. In the embodiment described previously, the four sided figures may be parallelograms and in yet another embodiment, a singe sensor or multiple sensors may be at least partially surrounded by a lattice-type arrangement of conductive traces. Conductive traces extend from the conductive members to a connecting end of the sensors and extend along the outside edges of the conductive members. They may be typically divided into two groups, one with an equal number of traces and the other with an uneven number of traces.

In yet another embodiment, the array of sensors, or in certain instances, a single sensor, may be surrounded by a ground grid that may be considered as a lattice, which includes a plurality of conductive traces arranged in a diagonally intersecting fashion. This lattice network defines a ground shield that surrounds the conductive member(s). The ground shield is connected to the connecting end of the sensor by way or one or more conductive traces for connection to a processor.

These and other objects, features and advantages of the Present Disclosure will be clearly understood through a consideration of the following detailed description.

BRIEF DESCRIPTION OF THE FIGURES

The organization and manner of the structure and operation of the Present Disclosure, together with further objects and advantages thereof, may best be understood by reference to the following Detailed Description, taken in connection with the accompanying Figures, wherein like reference numerals identify like elements, and in which:

FIG. 2 is a top plan view of one embodiment of the fluid sensor of FIG. 1, which utilizes a plurality of four-sided conductive members arranged in an angular orientation along a flexible substrate;

FIG. 3 is a top plan view of a second embodiment of the fluid sensor of FIG. 1, which utilizes a series of chevron-shaped conductive members arranged along a longitudinal axis of a flexible substrate;

DESCRIPTION OF THE PREFERRED EMBODIMENTS

While the Present Disclosure may be susceptible to embodiment in different forms, there is shown in the Figures, and will be described herein in detail, specific embodiments, with the understanding that the Present Disclosure is to be considered an exemplification of the principles of the Present Disclosure, and is not intended to limit the Present Disclosure to that as illustrated.

As such, references to a feature or aspect are intended to describe a feature or aspect of an example of the Present Disclosure, not to imply that every embodiment thereof must have the described feature or aspect. Furthermore, it should be noted that the description illustrates a number of features. While certain features have been combined together to illustrate potential system designs, those features may also be used in other combinations not expressly disclosed. Thus, the depicted combinations are not intended to be limiting, unless otherwise noted.

In the embodiments illustrated in the Figures, representations of directions such as up, down, left, right, front and rear, used for explaining the structure and movement of the various elements of the Present Disclosure, are not absolute, but relative. These representations are appropriate when the elements are in the position shown in the Figures. If the description of the position of the elements changes, however, these representations are to be changed accordingly.

Figure 1:
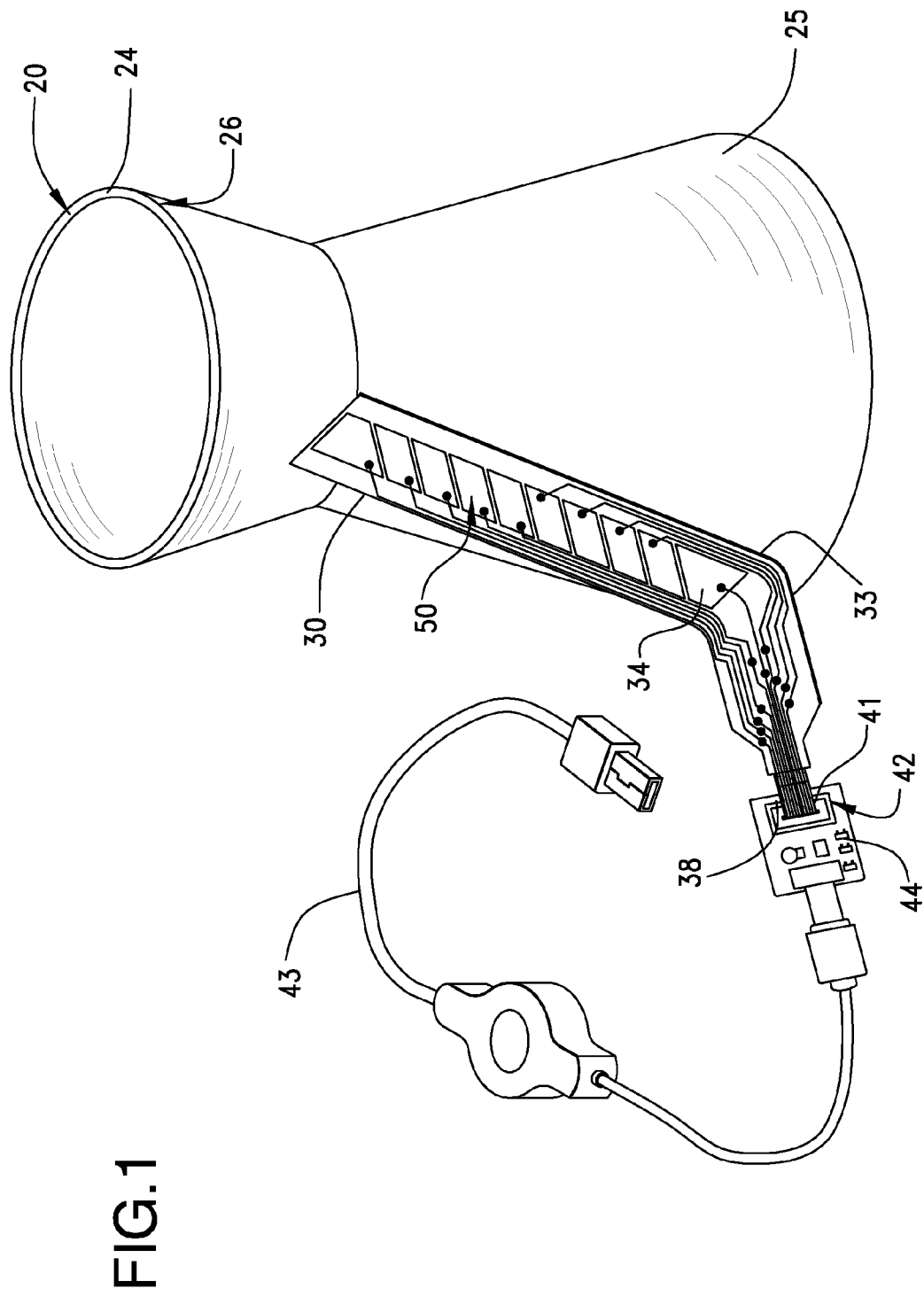
FIG. 1 is a perspective view of an irregularly-shaped fluid container with a fluid sensor constructed in accordance with the principles of the Present Disclosure in place on an exterior surface thereof.

FIG. 1 is a perspective view of a fluid container 20 and a fluid sensor 22 constructed in accordance with the principles of the Present Disclosure. As can be seen, the fluid container 20 takes the form of a beaker 24 having a wide base portion 25 that narrows in diameter as it rises vertically to a narrow neck portion 26 before is expands radially outwardly to form a lip portion 27. The container 20 is made from glass, plastic or another non-conductive material. Typically, such containers are provided in a "graduated" form; that is, it will have a series of horizontal level lines that are formed on its sidewall either by etching or printing. One may determine the level of a fluid within the container 20 by looking at the side of container. Such a reading is accomplished only by viewing the container 20 and such a determination requires that the container be placed on a level surface. Moreover, it is difficult to automate a visual reading of the fluid level. Accordingly, the Present Disclosure is directed to a fluid level sensor that is prone to easy automated readings and is capable of being utilized with a variety of irregularly-shaped fluid containers.

FIG. 2 illustrates, in plan view, a capacitive fluid level sensor 22 of the Present Disclosure. As illustrated, the sensor 22 is formed as an elongated strip 30 and has a non-conductive, dielectric substrate 32 that serves as a base portion of the sensor 22. The substrate 32 has two opposing sides, or surfaces 33, 34, one of which, 33, is a mounting side that is intended to be attached directly to the exterior of the fluid container 20. The substrate 32 is preferably formed from an inexpensive flexible dielectric material, such as polyester. A polyester substrate also permits the conductive member members to be easily applied to the substrate 32, such as by screen printing or other suitable means.

Figure 2A:
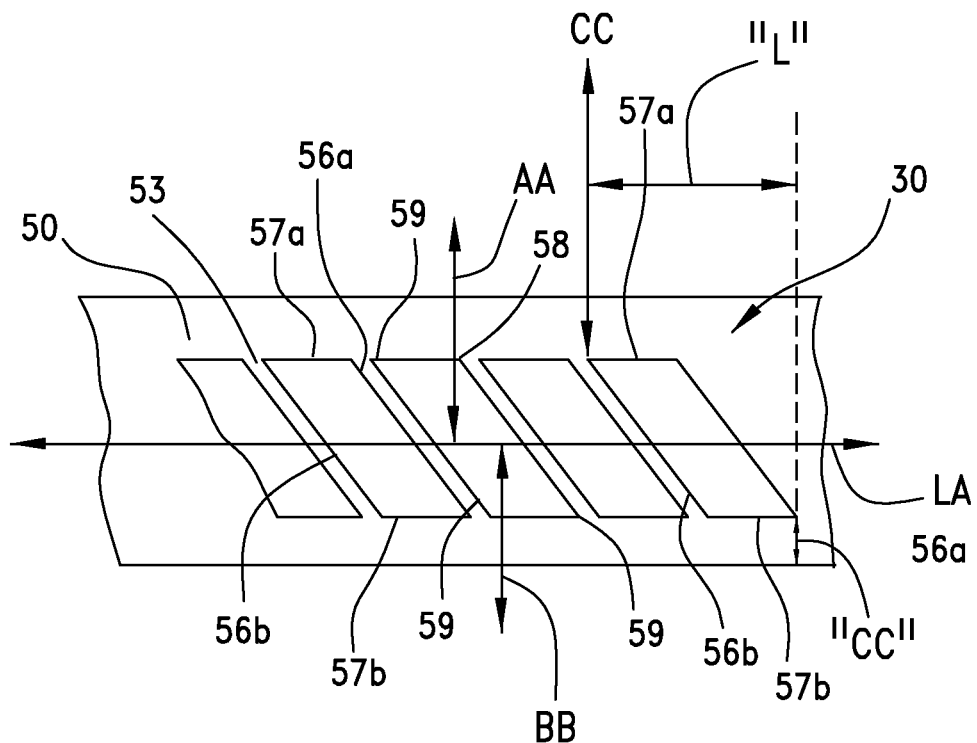
FIG. 2A is an enlarged detail view of a portion of FIG. 2, showing the overlapping array of conductive members within the sensor.
Figure 2B:
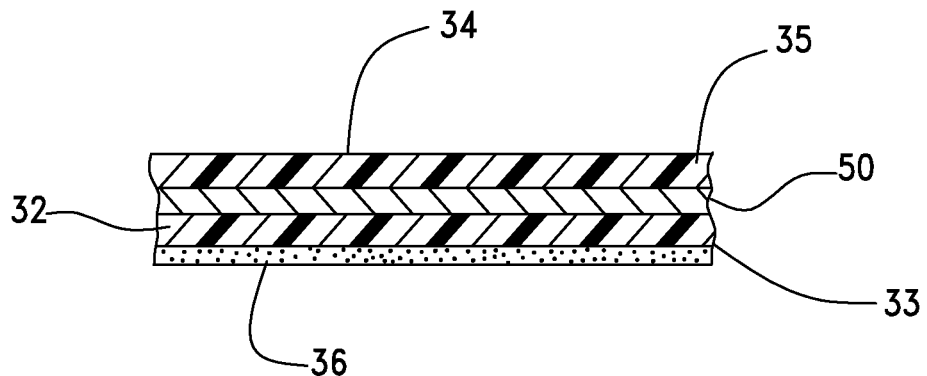
FIG. 2B is a sectional view taken of a portion of the sensor at "B" of FIG. 2.

The sensor 22, as best shown in the sectional view of FIG. 2B, may further include a cover layer 35 applied to the upper surface 34 of the substrate 32, and serves to isolate the conductive members 50 between two dielectric layers. A layer 36 of a pressure sensitive adhesive may be applied to the bottom, or mounting, surface 33 of the substrate 32 so that the sensor 22 may be applied to a container 20. In particular, the flexible nature of the substrate 22 permits it to be applied to irregularly shaped containers such as the beaker. Alternatively, intravenous plastic bags (not shown) or other type containers may also be used. A non-conductive backing member 37 may be provided at the connecting end 38 of the substrate 32, where the width is sufficiently narrowed to form a sensor insertion end that contains a plurality of contact pads 40 and which may be inserted into a receiving slot 41 of a receptacle connector 42, may be provided as part of an overall fluid level detection system that may be plugged into a computer or processor mounted on a small circuit board 44 by way of an appropriate connection means, such as the USB cable 43 shown. The adhesive layer 36 permits the substrate 32 to be applied to the exterior surface of a container 20 and especially an irregularly-shaped container such as the beaker 24 shown in FIG. 1.

In order to determine the fluid level, the sensor is provided with a plurality of conductive members, or electrodes, generally, 50, and specifically in FIG. 2, 50a-50j are arranged in a given pattern, or array 51. In each such arrangement, the conductive members 50 are separated from each other by intervening spaces 52. Further, as shown in a first embodiment as illustrated in FIG. 2, the conductive members 50 include a plurality of four-sided members 53. The conductive members 50 in this embodiment are of two types. The first type of conductive members 50a, 50j are those found at the opposite ends 54 of the array 51 and shall be referred to herein as "end" conductive members, while the second type of conductive members 50b-50i are those members that are included between the end members, and shall be referred to herein as "included" conductive members. The conductive members 50b and 50i that make up the ends of the included members may be referred to as "penultimate" conductive members. The included conductive members preferably are all identical to each other and more preferably they are all parallelograms having perimeters, or boundaries, made up of opposing ends 56a, 56b and opposing sides 57a, 57b that are joined together at respective inner and outer corners 58, 59. The resulting four-sided configurations of the conductive members are more diamond or rhombus-like shapes rather than rectangles.

It is desirable to have the included conductive members 50b-50i arranged so that their intervening spaces 53 intersect the chosen longitudinal axis LA of the substrate 32, or sensor 22, at an angle and the angle is chosen so that preferably, as illustrated in FIG. 2A the inner corners 58 are spaced apart from each other, or in other words, Lines AA and BB drawn through the inner corners 58 and normal to the longitudinal axis LA are not coincident, but rather, are spaced apart. Similarly, any line drawn within the body of an included conductive member 50b-50i, in a direction normal to the substrate longitudinal axis LA will contact, or intersect two adjacent conductive members. In this fashion, the conductive members 50 may be considered as overlapping each other, when viewed from a side edge of the substrate 32, or in other words, the intervening spaces 53 provide no clear path that intersects the longitudinal axis LA in a direction normal to the axis LA. This permits the capacitive measurement aspect to work along the entire array 51 of conductive members 50 without any interruption as may occur were the intervening spaces to be arranged normal to the longitudinal axis LA. The sensor 22 relies upon an inherent, parasitic capacitance to provide its level measurement function in that each conductive member 50 acts as a single plate of a capacitor with the surrounding material and circuitry coupled to ground as the other plate, in a manner different from sensors in the art that use a pair of plates for each conductive member. The conductive members 50 may be formed by screen printing a silver-based or other conductive ink on the substrate 32 or by stamping them out of a thin metal sheet stock and embedding the, in the substrate 32, or any other suitable manner.

The angled orientation of the conductive members 50 not only provides the overlap mentioned above but also increases the accuracy of the level measurement. The accuracy obtained within each conductive member may have a tolerance or 5% or the like, but that is within the length "L" of the conductive member, namely, the area that lies between imaginary lines CC drawn normal to the outer corners of the included conductive members 50b-50i. By containing the tolerance within each conductive member, the overall level is reduced by the tolerance of each conductive member divided by the total number of conductive members. In this manner, the measurement accuracy of the sensor is greatly increased. A plurality of conductive traces 60 are arranged on the substrate and are provided to connect the conductive members 50 with contact pads at the connecting end of the sensor. As shown the traces 60 may be arranged in two groups and they can extend, as illustrated along both sides of the array of conductive members. The traces may be arranged in even groups or one group with an even number of traces and the other group with an odd number of traces. Alternatively, the traces may be arranged in their own layer underneath the conductive members and insulated therefrom.

FIG. 3 illustrates another embodiment of a sensor 80 of the Present Disclosure in which the conductive members 82 have five and six-sided configurations. The conductive members 82a-j include end members 82a, 82j, each of which includes a five-sided figure and a series of included conductive members 82b-82i, each of which includes a six-sided figure and each of which are preferably identical to each other. In this embodiment, the conductive members 82 are aligned along a longitudinal axis of the substrate and are spaced apart from each other by intervening spaces 84. The spaces 84 are angled as in the first embodiment but in this embodiment they extend in two different directions, thereby giving the conductive members 82, at least the included conductive members 82b-82i chevron-like configurations. Each such included conductive member 82b-82i has a chevron configuration with a top portion 85 that is nested within a valley portion of an adjacent conductive member. As such, adjacent conductive members overlap each other when viewed from the side of the substrate in a direction normal to the longitudinal axis of the substrate. Conductive traces 87 are provided to connect the conductive members 80 to contact pads on the connecting end of the sensor 80.

Figure 4:
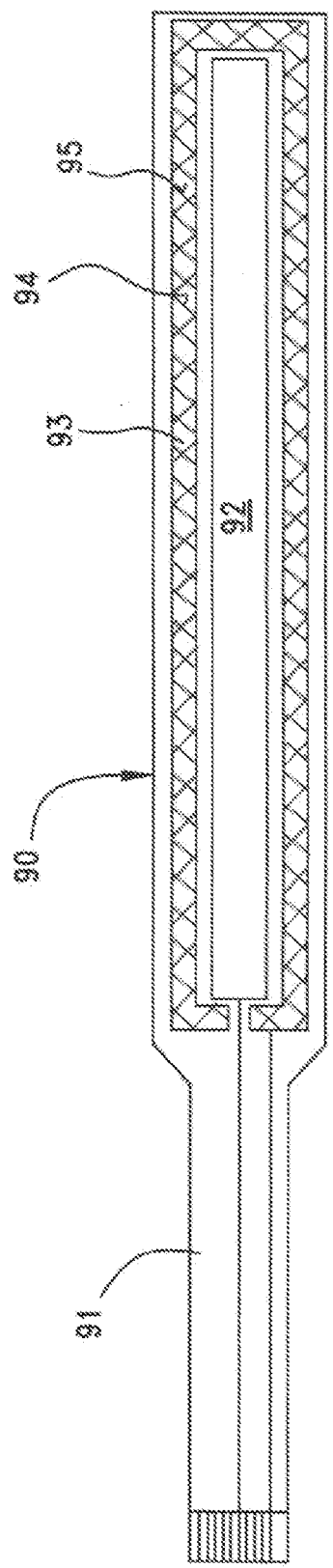
FIG. 4 is a top plan view of yet another embodiment of the fluid sensor of FIG. 1, which utilizes a single conductive member surrounded by a lattice, or angled grid, of conductive traces which are interconnected to form a ground shield.
Figure 5:
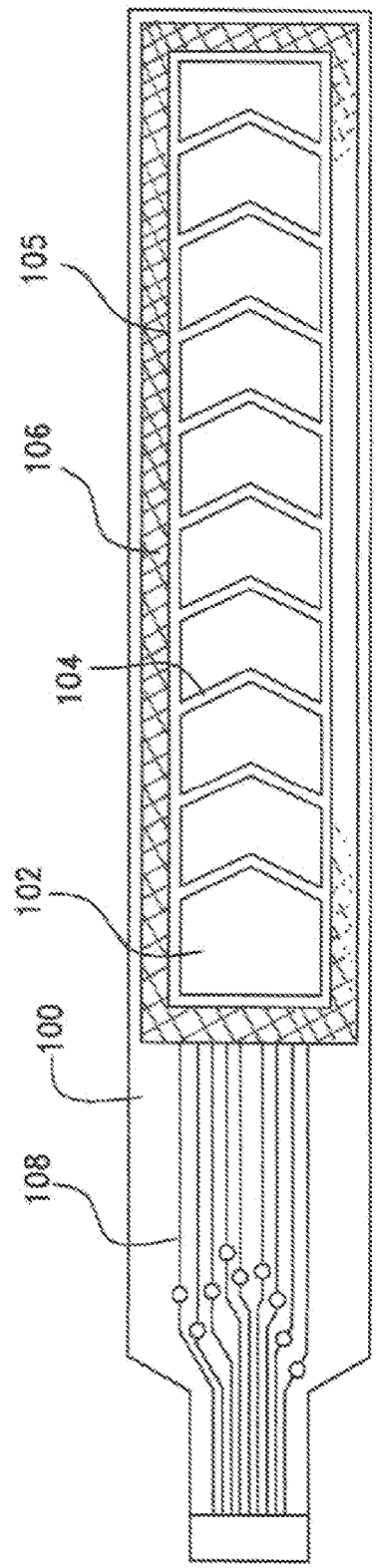
FIG. 5 is a top plan view of another embodiment of the fluid sensor of FIG. 1, utilizing a ground grid as a shield in the manner of the embodiment of FIG. 4, but which utilizes an array of conductive members as its sensor.

Another embodiment of a sensor 90 is illustrated in FIG. 4, which includes a substrate 91, and an elongated, four-sided conductive member 92 that is surrounded by a conductive grid, or lattice 93. The grid 93 is composed of a plurality of conductive traces 94 that are organized in an angular or diagonally interconnected relationship defining a network of openings 95 between the traces 94. The grid 93 is typically connected to a ground contact pad on the connecting end of the sensor 90 so that the grid 93 may act as the second plate of a capacitive pair with the conductive member 92. FIG. 5 illustrates another variant of a sensor 100 that utilizes the array of chevron-shaped conductive members 102 shown earlier that are aligned along a longitudinal axis and which are separated by intervening spaces 104. A conductive grid 105 is provided that encircles the array of conductive members 102 and the grid 105 has a lattice type configuration of a plurality of interconnected or intersecting traces 106, which define a series of enclosed openings. This grid 105 is connected to a ground terminal and acts as a second plate to the conductive members 102 in order to provide capacitive interaction between the two. Connecting traces 108 are provided to interconnect each conductive member 102 and the grid 105 to contact pads at a connecting end of the sensor. These connecting traces 108 run in a separate layer from the conductive members 102 and are insulated therefrom.

While a preferred embodiment of the Present Disclosure is shown and described, it is envisioned that those skilled in the art may devise various modifications without departing from the spirit and scope of the foregoing Description and the appended Claims.

What is claimed is:

1. A capacitive fluid level sensor assembly for sensing a level of a fluid within a vessel, the sensor assembly comprising:
   a substrate configured to be positioned alongside a wall of the vessel, such that the wall separates the substrate from the fluid, the substrate having upper and lower ends; and
   a plurality of conductive members supported by the substrate, the plurality of conductive members being provided between the upper and lower ends of the substrate, wherein the plurality of conductive members includes an upper end conductive member which is most proximate to the upper end of the substrate, a lower end conductive member which is most proximate to the lower end of the substrate, and at least one included conductive member which is positioned between the upper and lower end conductive members, wherein each conductive member is separated from an adjacent conductive member by an intervening space, thereby providing that each conductive member has distinct upper and lower ends and acts as an independent sensor which has a given measurement tolerance between the distinct upper and lower ends, wherein the distinct lower end of a lowermost included conductive member is positioned closer to the lower end of the substrate than the distinct upper end of the lower end conductive member.

2. The capacitive fluid level sensor assembly as defined in claim 1, wherein the distinct upper end of an uppermost included conductive member is positioned closer to the upper end of the substrate than the distinct lower end of the upper end conductive member.

3. The capacitive fluid level sensor assembly as defined in claim 2, wherein the distinct upper end of the uppermost included conductive member is at least one point.

4. The capacitive fluid level sensor assembly as defined in claim 2, wherein the distinct lower end of the upper end conductive member is at least one point.

5. The capacitive fluid level sensor assembly as defined in claim 2, wherein the uppermost included conductive member and the lowermost included conductive member are not the same.

6. The capacitive fluid level sensor assembly as defined in claim 1, wherein the distinct lower end of the lowermost included conductive member is at least one point.

7. The capacitive fluid level sensor assembly as defined in claim 1, wherein the distinct upper end of the lower end conductive member is at least one point.

8. The capacitive fluid level sensor assembly as defined in claim 1, wherein the substrate is formed from a flexible dielectric material.

9. The capacitive fluid level sensor assembly as defined in claim 1, wherein each conductive member has a plate-like configuration.

10. The capacitive fluid level sensor assembly as defined in claim 1, wherein the plurality of conductive members are provided in an array between the upper and lower ends of the substrate.

11. The capacitive fluid level sensor assembly as defined in claim 10, wherein each of the upper end conductive member and the at least one included conductive member have sides which are planar to one another in a longitudinal direction.

12. The capacitive fluid level sensor assembly as defined in claim 10, wherein each of the lower end conductive member and the at least one included conductive member have sides which are planar to one another in a longitudinal direction.

13. The capacitive fluid level sensor assembly as defined in claim 10, wherein each of the lower end conductive member and the upper end conductive member have sides which are planar to one another in a longitudinal direction.

14. The capacitive fluid level sensor assembly as defined in claim 1, wherein a cover layer seals the plurality of conductive members to the substrate.

15. The capacitive fluid level sensor assembly as defined in claim 1, wherein a layer of pressure-sensitive adhesive is applied to at least a portion of a mounting side of the substrate.

16. The capacitive fluid level sensor assembly as defined in claim 1, wherein the upper end conductive member has a configuration which is different from a configuration of the at least one included conductive member.

17. The capacitive fluid level sensor assembly as defined in claim 1, wherein the lower end conductive member has a configuration which is different from a configuration of the at least one included conductive member.

18. The capacitive fluid level sensor assembly as defined in claim 1, wherein the upper end conductive member has a configuration which is different from a configuration of the lower end conductive member.

19. The capacitive fluid level sensor assembly as defined in claim 1, wherein the intervening space separating adjacent conductive members intersect a longitudinal axis of the substrate at an angle.

20. The capacitive fluid level sensor assembly as defined in claim 1, wherein the substrate defines a longitudinal axis which extends from the upper end thereof to the lower end thereof, and wherein any imaginary line drawn normal to the longitudinal axis which intersects an included conductive member also intersects one of the upper end conductive member, the lower end conductive member, and another one of the included conductive members.

21. The capacitive fluid level sensor assembly as defined in claim 1, wherein the at least one included conductive member is four-sided.

22. The capacitive fluid level sensor assembly as defined in claim 21, wherein the at least one included conductive member is in the form of a parallelogram.

23. The capacitive fluid level sensor assembly as defined in claim 1, wherein the at least one included conductive member is six-sided.

24. The capacitive fluid level sensor assembly as defined in claim 23, wherein the at least one included conductive member is in the form of a chevron.

25. The capacitive fluid level sensor assembly as defined in claim 1, wherein the intervening space separating adjacent conductive members extends in two different directions.

26. The capacitive fluid level sensor assembly as defined in claim 1, wherein the substrate has an insertion portion which is configured to be inserted into a receiving slot of a receptacle connector.

27. The capacitive fluid level sensor assembly as defined in claim 26, wherein the insertion portion of the substrate contains a plurality of contact pads which are electrically connected to the plurality of conductive members.

28. The capacitive fluid level sensor assembly as defined in claim 26, wherein the insertion portion of the substrate is provided at one of the upper and lower ends of the substrate.

29. The capacitive fluid level sensor assembly as defined in claim 1, wherein each conductive member is electrically connected to circuitry of a readout or processor.

30. A capacitive fluid level sensor assembly for sensing a level of a fluid within a vessel, the sensor assembly comprising:
a substrate configured to be positioned alongside a wall of the vessel, such that the wall separates the substrate from the fluid, the substrate having upper and lower ends; and
a plurality of conductive members supported by the substrate, the plurality of conductive members being provided between the upper and lower ends of the substrate, wherein the plurality of conductive members includes an upper end conductive member which is most proximate to the upper end of the substrate, a lower end conductive member which is most proximate to the lower end of the substrate, and at least one included conductive member which is positioned between the upper and lower end conductive members, wherein each conductive member is separated from an adjacent conductive member by an intervening space, thereby providing that each conductive member has distinct upper and lower ends and acts as an independent sensor which has a given measurement tolerance between the distinct upper and lower ends, wherein the distinct upper end of an uppermost included conductive member is positioned closer to the upper end of the substrate than the distinct lower end of the upper end conductive member.

31. The capacitive fluid level sensor assembly as defined in claim 30, wherein the distinct upper end of the uppermost included conductive member is at least one point.

32. The capacitive fluid level sensor assembly as defined in claim 30, wherein the distinct lower end of the upper end conductive member is at least one point.

33. The capacitive fluid level sensor assembly as defined in claim 30, wherein the uppermost included conductive member and the lowermost included conductive member are not the same.

34. A capacitive fluid level sensor assembly for sensing a level of a fluid within a vessel, the sensor assembly comprising:
a substrate configured to be positioned alongside a wall of the vessel, such that the wall separates the substrate from the fluid, the substrate having upper and lower ends; and
a plurality of conductive members supported by the substrate, the plurality of conductive members being provided between the upper and lower ends of the substrate, wherein the plurality of conductive members includes an upper end conductive member which is most proximate to the upper end of the substrate, a lower end conductive member which is most proximate to the lower end of the substrate, and at least one included conductive member which is positioned between the upper and lower end conductive members, wherein each conductive member is separated from an adjacent conductive member by an intervening space, thereby providing that each conductive member has distinct upper and lower ends and acts as an independent sensor which has a given measurement tolerance between the distinct upper and lower ends, wherein at least one pair of adjacent conductive members are positioned relative to each other such that the distinct lower end of one of the adjacent conductive members is positioned lower than the distinct upper end of the other one of the adjacent conductive members.

35. The capacitive fluid level sensor assembly as defined in claim 34, wherein the at least one pair of adjacent conductive members includes the upper end conductive member and an uppermost included conductive member.

36. The capacitive fluid level sensor assembly as defined in claim 34, wherein the at least one pair of adjacent conductive members includes the lower end conductive member and a lowermost included conductive member.

37. The capacitive fluid level sensor assembly as defined in claim 34, wherein the at least one pair of adjacent conductive members includes two included conductive members.

38. The capacitive fluid level sensor assembly as defined in claim 34, wherein all adjacent conductive members are positioned relative to each other such that the distinct lower end of one of the adjacent conductive members is positioned lower than the distinct upper end of the other one of the adjacent conductive members.

39. A capacitive fluid level sensor assembly for sensing a level of a fluid within a vessel, the sensor assembly comprising:
a substrate configured to be positioned alongside a wall of the vessel, such that the wall separates the substrate from the fluid, the substrate having upper and lower ends;
a plurality of conductive members supported by the substrate, the plurality of conductive members being provided in an array between the upper and lower ends of the substrate, each conductive member being separated from an adjacent conductive member, each conductive member having a distinct upper end and a distinct lower end, wherein at least one pair of adjacent conductive members are positioned relative to each other such that the distinct lower end of one of the adjacent conductive members is positioned lower than the distinct upper end of the other one of the adjacent conductive members, each conductive member having a first measurement tolerance between the distinct upper and lower ends;
electronics which are electrically connected to each conductive member, the electronics configured to measure a capacitance of each conductive member, which measured capacitance corresponds to the level of fluid within the vessel according to the respective conductive member within the first measurement tolerance, the electronics further configured to divide the first measurement tolerance by the total number of conductive members in order to define an overall level of fluid within the vessel within a second measurement tolerance, where the second measurement tolerance is lower than the first measurement tolerance.

* * * * *